United States Patent
Schütz et al.

(10) Patent No.: US 9,827,397 B2
(45) Date of Patent: Nov. 28, 2017

(54) ANTIMICROBIALLY ACTIVE WOUND DRESSING FOR CATHETER FIXINGS

(71) Applicant: BSN medical, GmbH, Hamburg (DE)

(72) Inventors: Patrick Schütz, Hamburg (DE); Bettina Schultz, Hamburg (DE)

(73) Assignee: BSN MEDICAL GMBH, Hamburg (DE)

( * ) Notice: Subject to any disclaimer, the term of this patent is extended or adjusted under 35 U.S.C. 154(b) by 0 days.

(21) Appl. No.: 15/158,999

(22) Filed: May 19, 2016

(65) Prior Publication Data

US 2016/0263351 A1 Sep. 15, 2016

Related U.S. Application Data

(63) Continuation of application No. 14/147,804, filed on Jan. 6, 2014, now Pat. No. 9,393,163.

(30) Foreign Application Priority Data

Jan. 8, 2013 (EP) .................................... 13150513

(51) Int. Cl.
| | | |
|---|---|---|
| A61F 13/00 | (2006.01) | |
| A61M 25/02 | (2006.01) | |
| A61F 13/02 | (2006.01) | |
| A61F 13/84 | (2006.01) | |
| A61M 16/04 | (2006.01) | |

(52) U.S. Cl.
CPC ....... *A61M 25/02* (2013.01); *A61F 13/00991* (2013.01); *A61F 13/022* (2013.01); *A61F 13/0203* (2013.01); *A61F 13/025* (2013.01); *A61F 13/0213* (2013.01); *A61F 13/0246* (2013.01); *A61F 13/0266* (2013.01); *A61F 13/84* (2013.01); *A61F 2013/00319* (2013.01); *A61F 2013/00336* (2013.01); *A61F 2013/00412* (2013.01); *A61M 16/047* (2013.01); *A61M 2025/0273* (2013.01)

(58) Field of Classification Search
CPC .......... A61F 13/00021; A61F 13/00063; A61F 13/00029; A61F 13/02; A61F 13/023; A61F 13/0246; A61F 2013/00604; A61M 1/0088; A61M 2025/0266; A61M 2025/0273
USPC ............ 424/447; 602/41–44, 48, 52, 54, 56; 604/180, 307, 543
See application file for complete search history.

(56) References Cited

U.S. PATENT DOCUMENTS

| | | | | |
|---|---|---|---|---|
| 5,447,492 A | * | 9/1995 | Cartmell ............. | A61F 13/0203 602/41 |
| 5,554,106 A | * | 9/1996 | Layman-Spillar .... | A61F 13/022 128/DIG. 26 |

(Continued)

OTHER PUBLICATIONS

European Search Report dated Mar. 27, 2013 for Patent Application No. EP 13 15 0513.

*Primary Examiner* — Gerald Landry, II
(74) *Attorney, Agent, or Firm* — Shumaker, Loop & Kendrick, LLP

(57) ABSTRACT

A multilayered wound dressing which is two-dimensional and has a peripheral edge is provided that includes at least one hydrophobic antimicrobial layer, at least one absorbent layer which includes a water-containing hydrogel, and a covering layer. Starting from the edge of the wound dressing, at least one incision is formed, which partially separates the wound dressing.

14 Claims, 8 Drawing Sheets

(56) References Cited

U.S. PATENT DOCUMENTS

| | | | |
|---|---|---|---|
| 5,973,221 A * | 10/1999 | Collyer | A61F 13/00034 602/46 |
| 6,160,196 A | 12/2000 | Knieler et al. | |
| 7,137,968 B1 * | 11/2006 | Burrell | A61M 25/02 602/54 |
| 8,778,387 B2 | 7/2014 | Tennican et al. | |
| 2004/0082925 A1 * | 4/2004 | Patel | A61L 15/44 604/289 |
| 2004/0247654 A1 * | 12/2004 | Asmus | A61K 9/0014 424/449 |
| 2004/0249328 A1 | 12/2004 | Linnane | |
| 2005/0010153 A1 * | 1/2005 | Lockwood | A61F 13/02 602/41 |
| 2006/0129080 A1 * | 6/2006 | Bjornberg | A61F 13/00042 602/41 |
| 2006/0155260 A1 | 7/2006 | Blott et al. | |
| 2007/0293800 A1 * | 12/2007 | McMaken | A61L 15/44 602/48 |
| 2010/0010462 A1 | 1/2010 | Kurata | |
| 2010/0022961 A1 * | 1/2010 | Dewey | A61F 13/023 604/180 |
| 2010/0198177 A1 * | 8/2010 | Yahiaoui | A61F 13/82 604/359 |
| 2010/0331785 A1 * | 12/2010 | Fabo | A61M 16/047 604/180 |
| 2011/0166492 A1 * | 7/2011 | Holm | A61L 15/46 602/43 |
| 2011/0224631 A1 | 9/2011 | Simmons et al. | |
| 2012/0004615 A1 * | 1/2012 | Schmidt | A61F 13/0203 604/174 |
| 2013/0110025 A1 * | 5/2013 | Donnellan | A61L 15/26 602/46 |
| 2013/0165865 A1 * | 6/2013 | Kelvered | A61M 25/02 604/180 |
| 2013/0189339 A1 * | 7/2013 | Vachon | A61K 31/167 424/404 |
| 2013/0274667 A1 * | 10/2013 | Conrad-Vlasak | A61F 13/00 604/117 |
| 2014/0005607 A1 * | 1/2014 | Elsamahy | A61M 25/02 604/180 |
| 2014/0046238 A1 * | 2/2014 | Leibowitz | A61F 13/00063 602/48 |
| 2015/0025436 A1 * | 1/2015 | Tang | A61M 25/02 602/43 |

* cited by examiner

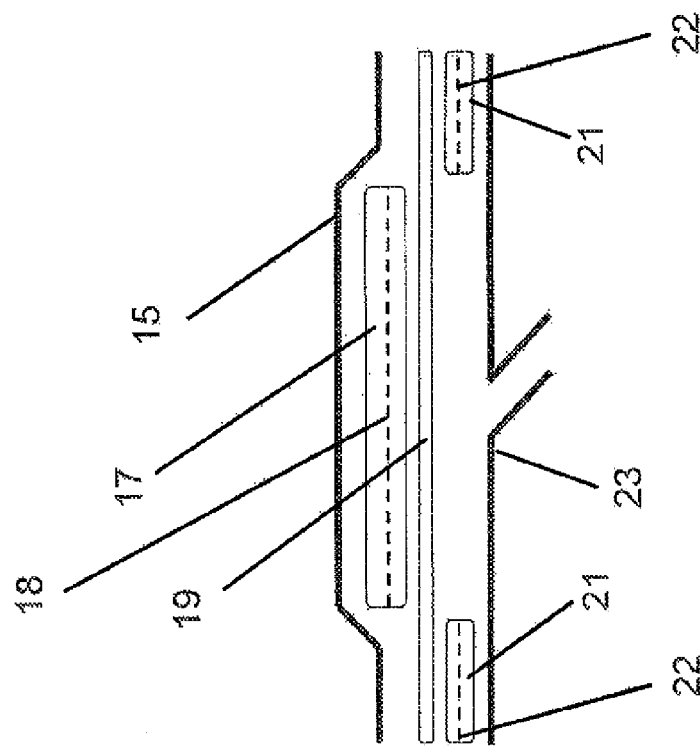
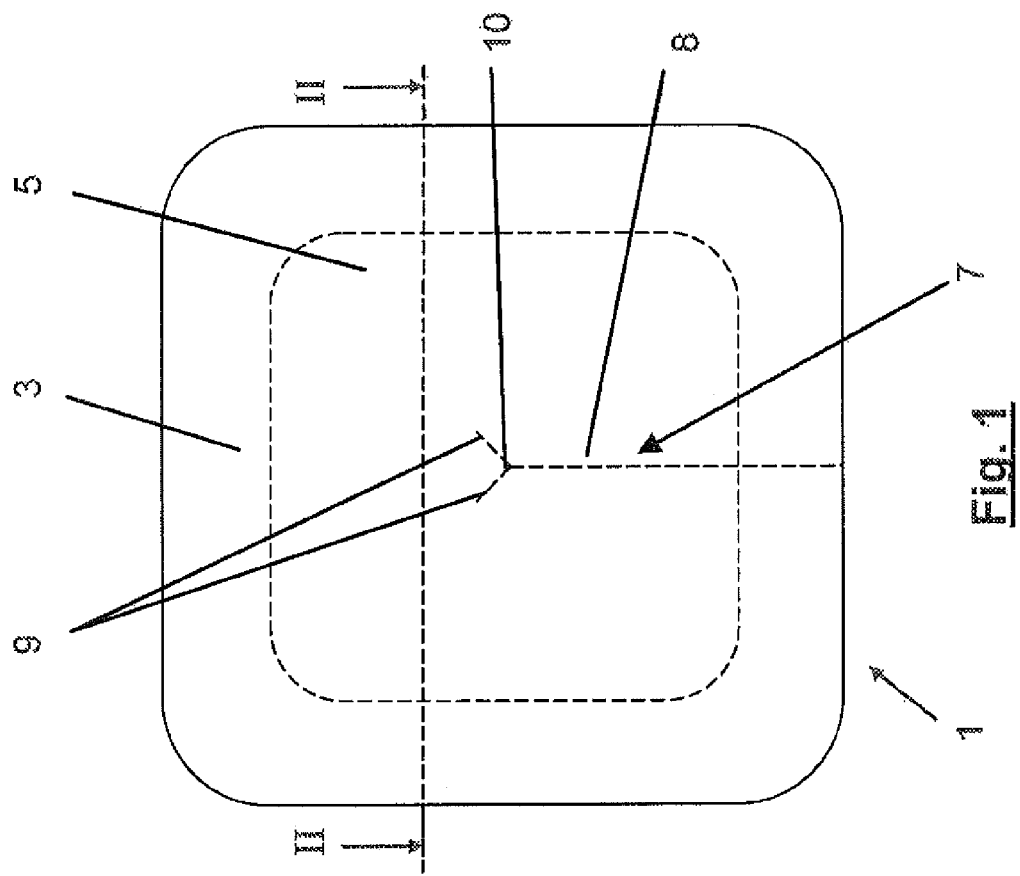

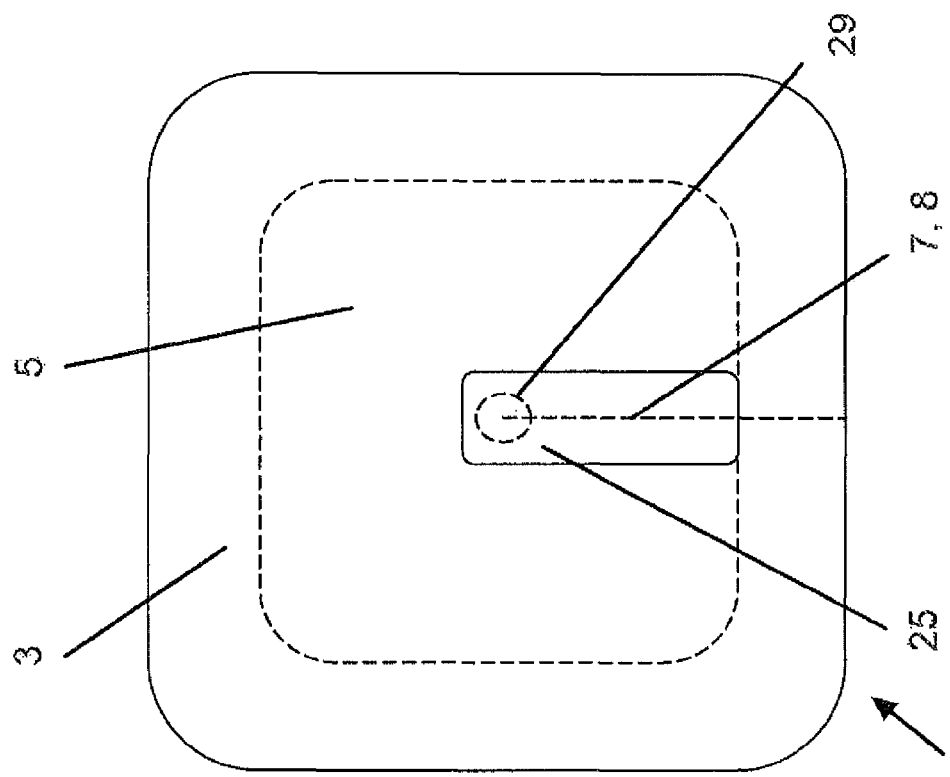
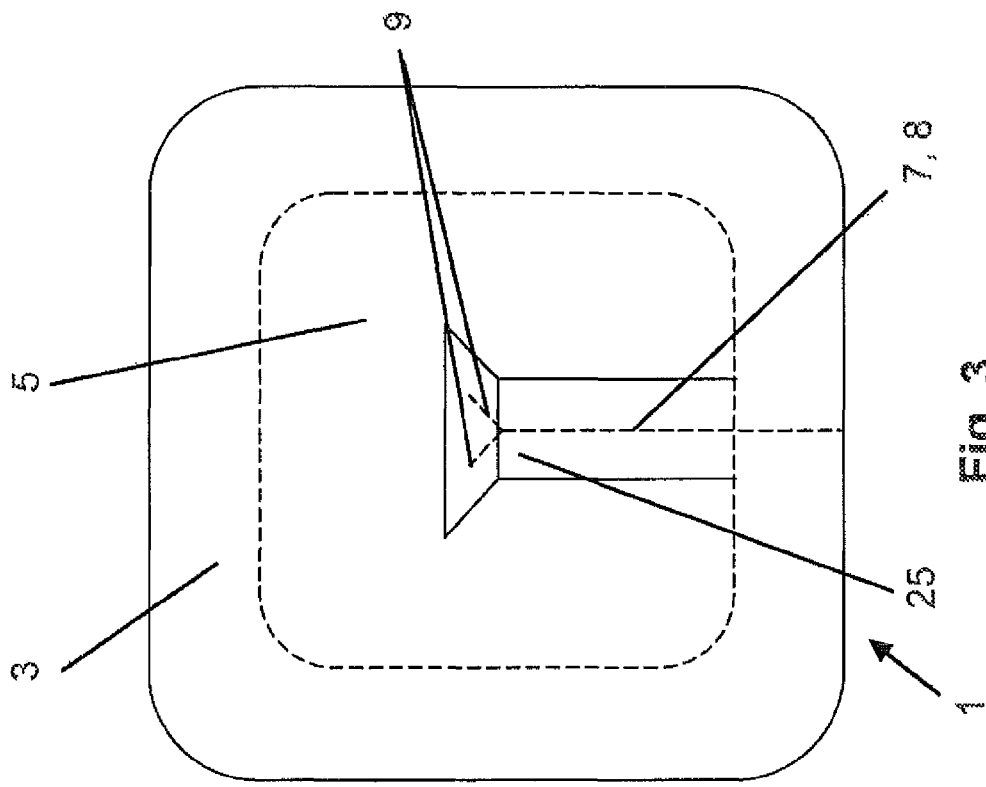

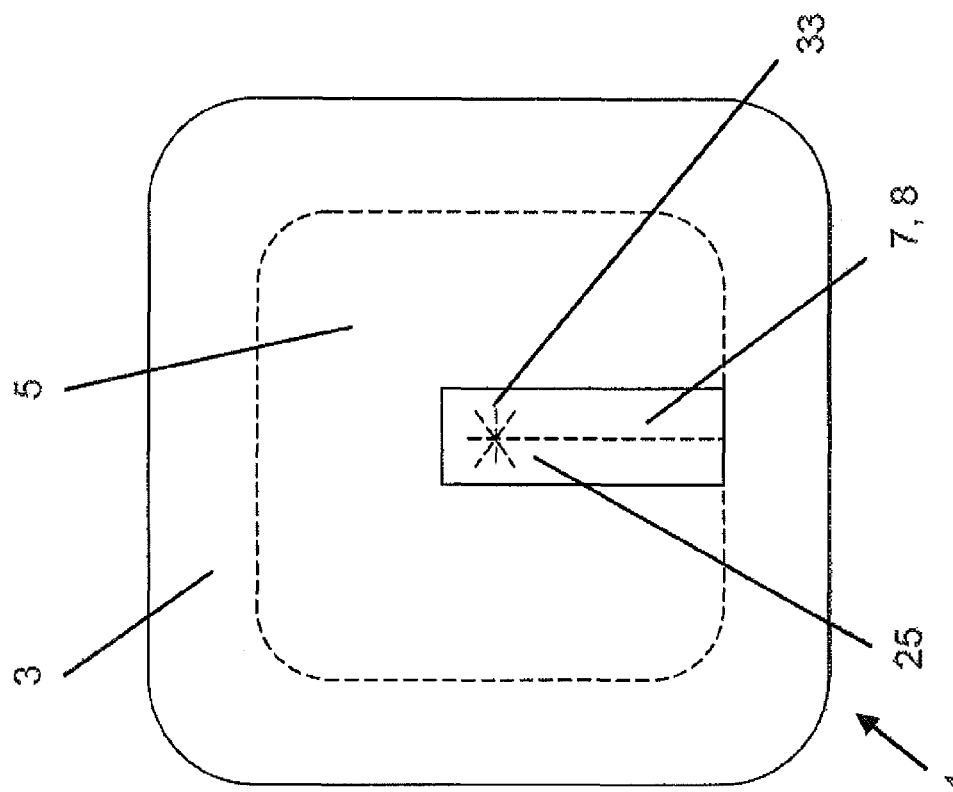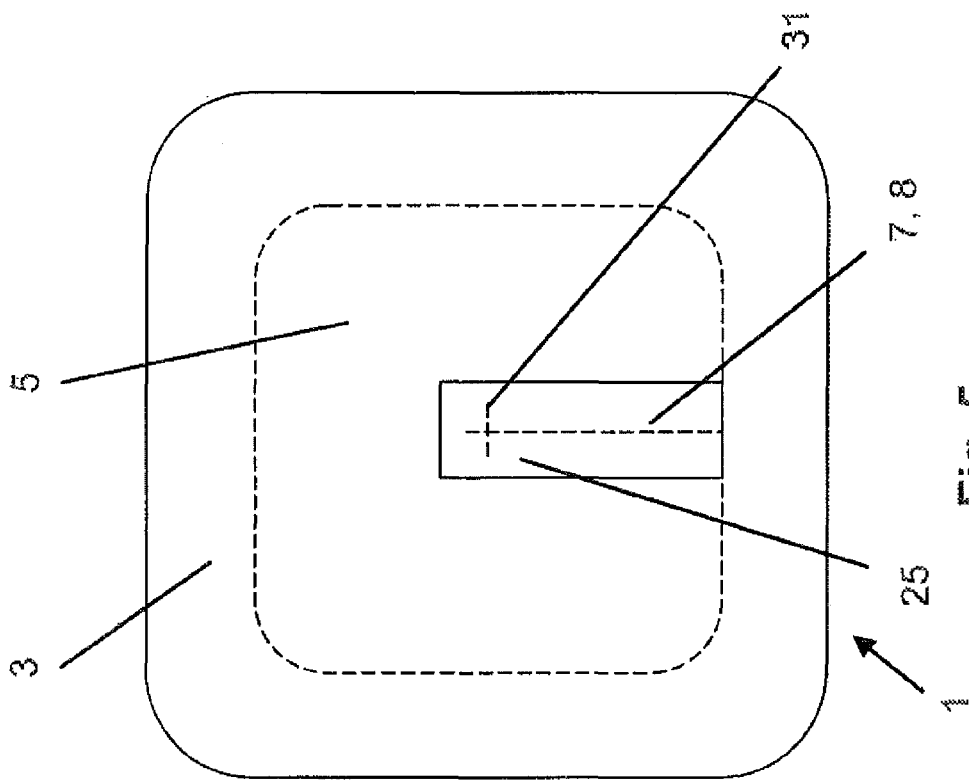

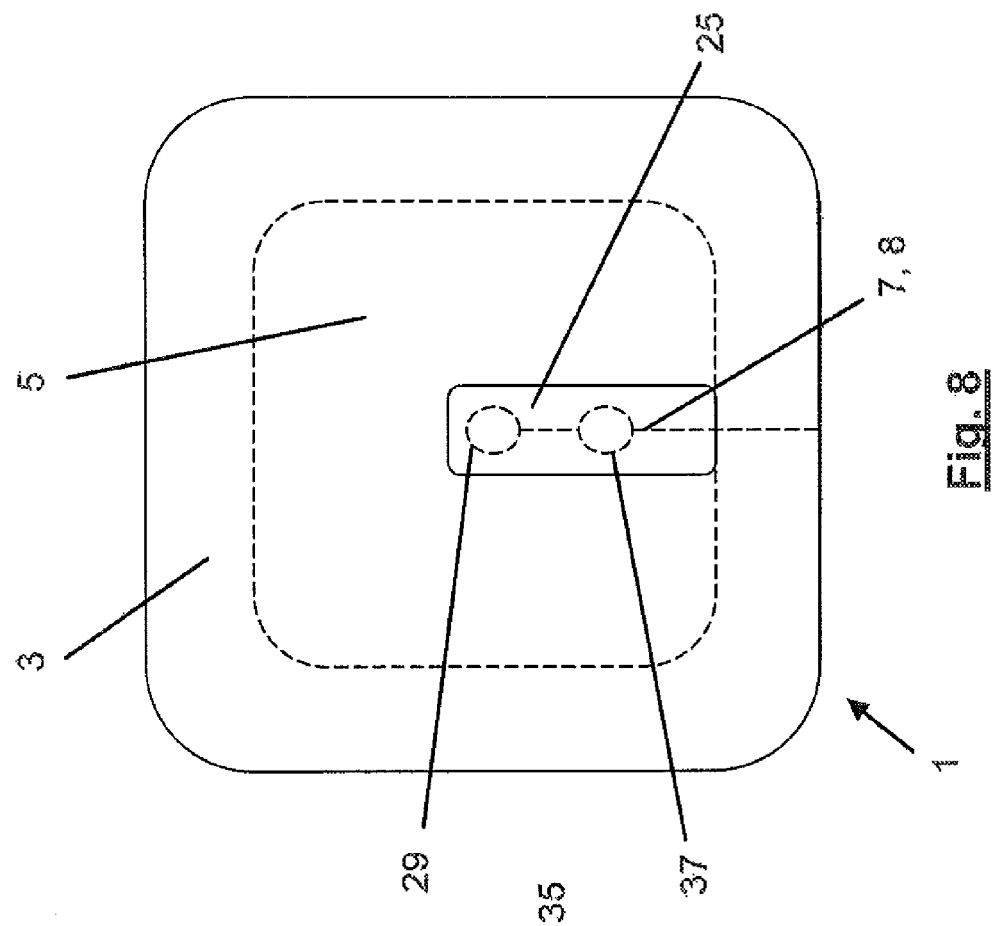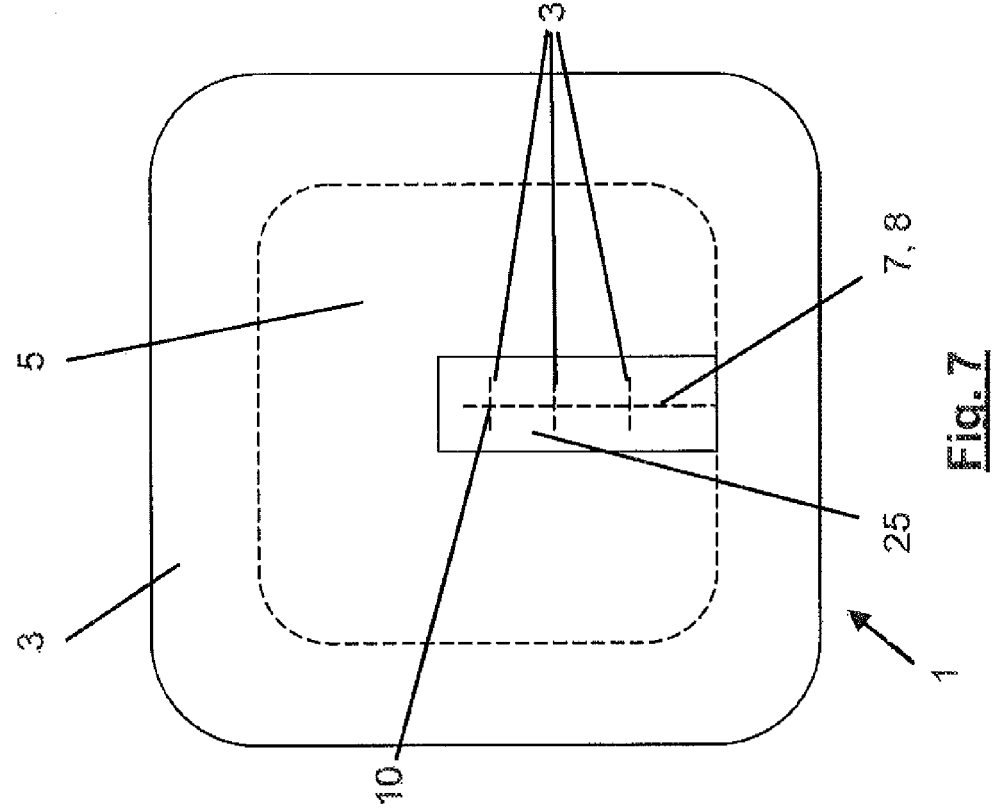

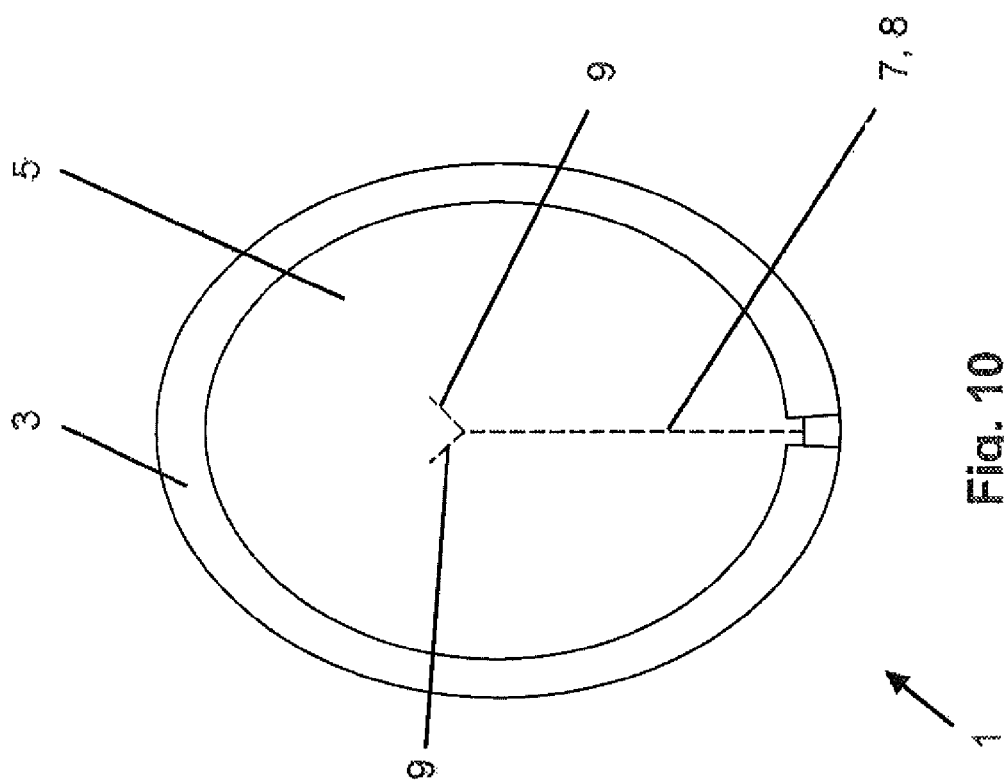
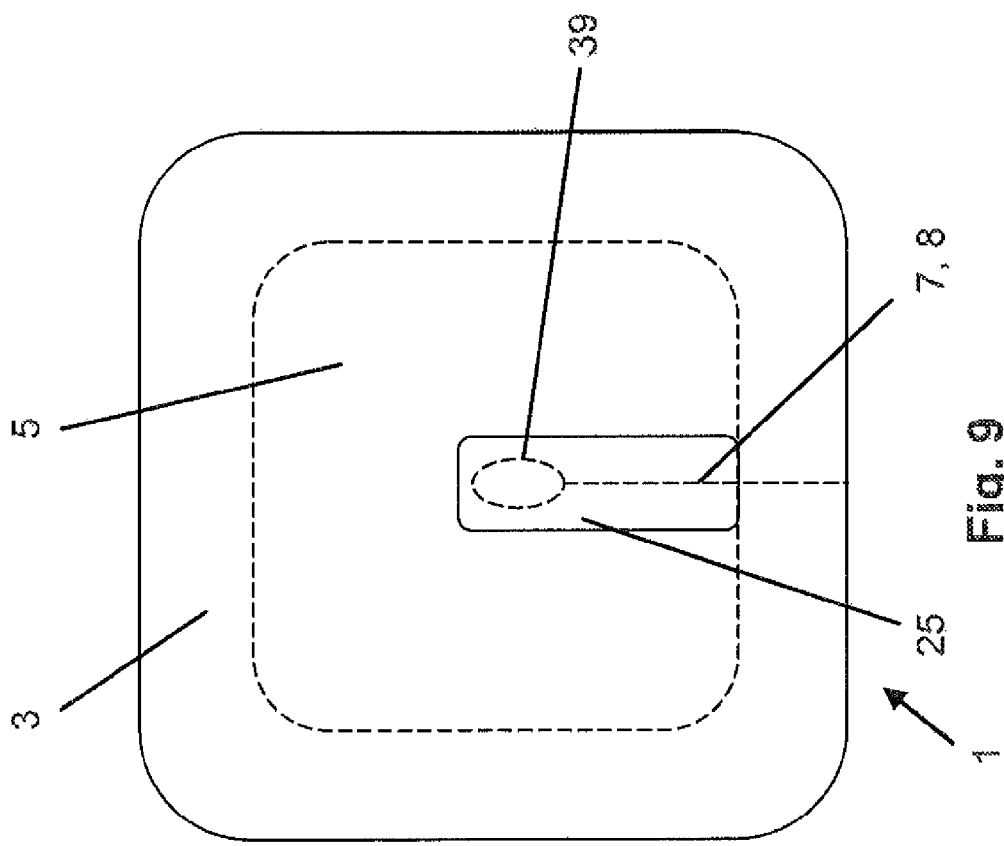

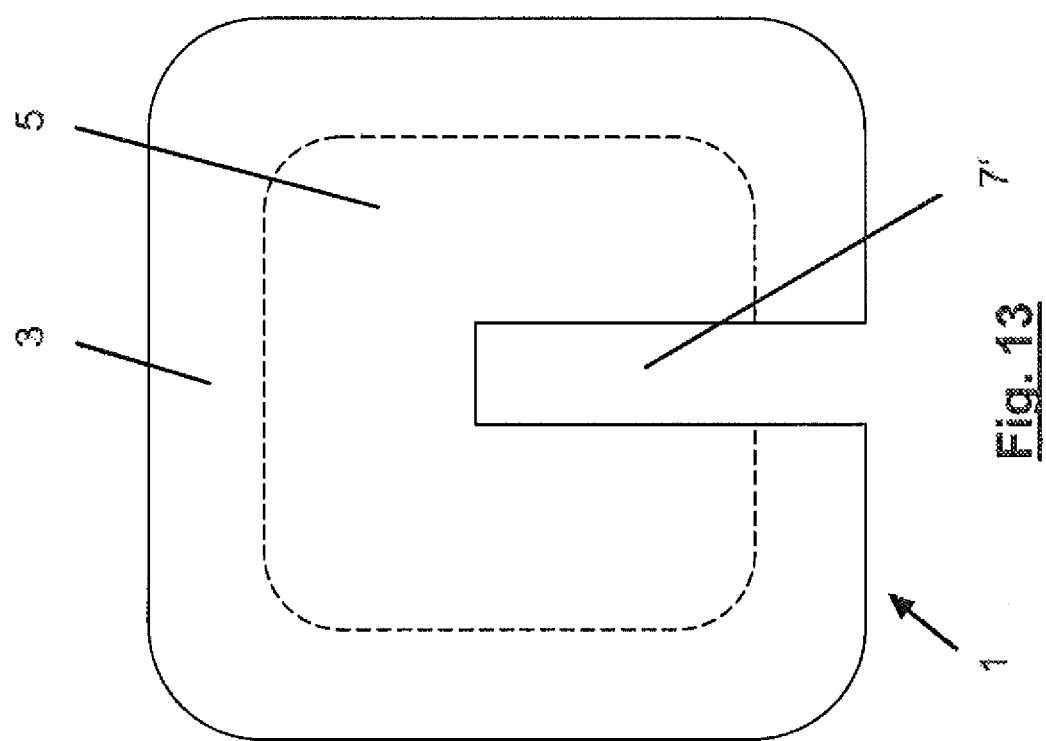

ANTIMICROBIALLY ACTIVE WOUND DRESSING FOR CATHETER FIXINGS

TECHNICAL FIELD AND BACKGROUND OF THE INVENTION

The present invention relates to a multilayered wound dressing and the use thereof for covering wounds, in particular for covering wound openings for lines and tubes leading into the body or out of the body, such as e.g. catheters.

Wound dressings, also known as gateway dressings, are known, and reused for fixing lines and tubes leading into or out of the body, for covering the wound opening caused by the lines or tubes and for absorbing wound secretions. For this purpose wound dressings of a nonwoven or a woven fabric, so-called gauze, are conventionally available as slit compresses which have one or more slits so that the wound dressing can be laid around lines or tubes from a human or animal body opening. The main task of such products lies in covering the wound opening. A disadvantage of known slit compresses is that they often close the wound opening only inadequately, and because of their limited absorption capacity for wound fluid have to be changed relatively frequently.

The present invention is thus based on the object of extending and improving the field of use of wound dressings, in particular wound dressings for wrapping around lines and tubes leading into the body or out of the body, such as, for example, catheters. In particular, a secure fixing of the lines and/or tubes is to be effected by the wound dressing according to the invention. Furthermore, the wound opening is to be covered as tightly as possible and the wearing time of the wound dressings is to be increased compared with the known wound coverings. The wound dressing moreover is to be antimicrobially active, in order to prevent infections, and is to fit the anatomy of the patient well, so that it can be easily applied.

SUMMARY OF THE INVENTION

It has now been found that these objects are achieved by a wound dressing having a multilayered wound dressing which is two-dimensional and has a peripheral edge. A preferred embodiment of the wound dressing includes at least one hydrophobic antimicrobial layer, at least one absorbent layer which comprises a water-containing hydrogel, and a covering layer.

The wound dressing according to one embodiment of the invention is furthermore characterized in that, starting from the peripheral edge of the wound dressing, at least one incision is formed which partially separates the wound dressing.

The incision and thus the partial separation of the wound dressing in particular is essentially effected perpendicularly to as to the above-described layers. It is furthermore particularly preferable for the above-described layers, and if appropriate further layers, which are described in the following, to be arranged essentially parallel one above the other.

According to a first preferred embodiment of the invention the wound dressing is characterized in that the edges of the wound dressing separated by the at least one incision lie directly adjacent to one another at least along a part of the length of the incision. It is particularly preferable for the edges of the wound dressing separated by the incision to lie directly adjacent to one another along the entire length of the incision.

According to another preferred embodiment of the invention, the wound dressing is characterized in that the at least one incision is formed as an elongated recess with edges running at a distance from one another. In this embodiment the incision thus forms an elongated recess, such as, for example, a U-shaped recess.

According to a further development of the invention, it may also be provided that the incision of the wound dressing has one or more openings, such as e.g. holes, which are arranged between the edge and the end of the incision at a distance from the edge. These openings can be, in particular, circular or ellipsoidal in structure and can have a diameter of from 0.5 to 10 mm, in particular 0.5 to 5 mm. Particularly preferably, the one or the several openings extend(s) through all the layers of the wound dressing. The purpose of the openings is such that the wound dressing can be fitted more easily to the cross-section of the tube which leads into the body or out of the body and is to be wrapped around.

In one embodiment of this further development the at least one incision of the wound dressing has at least one opening between the peripheral edge and the end thereof remote from the edge. For example, this opening is approximately at the halfway point between the edge and the end of the incision remote from the edge.

However, a wound dressing in which an opening is located at the end of the incision remote from the edge is preferred. A preferred embodiment of the invention thus relates to a wound dressing in which the incision has at least one opening at the end remote from the edge.

According to a further embodiment, it is preferable for the wound dressing to have, instead of the at least one opening or in addition to the at least one opening, transverse slits which run transversely to the at least one incision. Such transverse slits are located in particular in a main section of the incision which extends from the edge to an end remote from the edge. In one embodiment the wound dressing according to the invention is consequently characterized in that the at least one incision has a main section which extends from the edge to an end remote from the edge, and the main section has one or more transverse slits running transversely to the incision. In this embodiment it is very particularly preferable for the one or the several transverse slits running transversely to the incision to extend equally on both sides of the incision. The incision and the one or the several transverse slits running transversely to the incision can thus together form one or more cross-shaped cuts.

According to a further particularly preferred embodiment of the wound dressing according to the invention the at least one incision of the wound dressing has a main section which extends from the edge to an end remote from the edge, a multiplicity of slits extending away at the end of the main section remote from the edge. This multiplicity of slits can form, together with the main section, for example Y-shaped, T-shaped, star-shaped or cross-shaped cuts.

The main task of the incision of the wound dressing and of the openings, transverse slits and multiplicity of slits at the end of the incision remote from the edge which are discussed above and may be present is to achieve a good fit to the catheter tube, for example, and to the anatomical situation of the patient, so that the wound dressing can be easily laid around the lines and tubes leading into the body and out of the body and fits the topography of the patient well.

According to one embodiment the wound dressing is characterized in that the absorbent layer extends directly to the at least one incision. In this embodiment the edges of the absorbent layer which are separated by the incision thus lie directly adjacent to one another at least along a part of the length of the incision, preferably along essentially the entire length of the incision.

In another embodiment the wound dressing is characterized in that the absorbent layer has in the region of the incision a recess with edges running at a distance from one another. According to this embodiment the at least one incision of the wound dressing is thus surrounded by a region which is free from the absorbent layer. If the incision of the wound dressing has at least one opening or one or more transverse slits or a multiplicity of slits at the end at a distance from the edge, such as have been described above, this/these opening(s), transverse slits or multiplicity of slits can also be surrounded by a region which is free from the absorbent layer.

One layer of the wound dressing according to the invention is a hydrophobic antimicrobial layer. In particular, the hydrophobic antimicrobial layer may be a cellulose acetate fabric, viscose fabric, cotton fabric or a blended fabric, it being possible for melded fibers preferably to be used as the blended fabric. A hydrophobic antimicrobial layer based on cellulose acetate fabric and cotton fabric, in particular cellulose acetate fabric, is particularly preferred. The hydrophobizing of the hydrophobic antimicrobial layer can include a treatment with dialkylcarbamoyl chloride (DACC) and/or alkene ketene dimer. In a particularly preferred embodiment layer (a) comprises cellulose acetate fabric which is coated with DACC, such as dihexadecylcarbamoyl chloride or dioctadecylcarbamoyl chloride.

The hydrophobic antimicrobial layer preferably has a weight per unit area of from 40 to 80 g/m$^2$, in particular 54 to 66 g/m$^2$ and particularly preferably about 60 g/m$^2$. The thickness of the hydrophobic antimicrobial layer furthermore is preferably 0.2 to 1.0 mm.

One layer of the wound dressing according to the invention is an absorbent layer which comprises a water-containing hydrogel. In a particular embodiment the hydrogel comprises so-called superabsorbent polymers and in particular polymers which have hydroxyl, carboxyl, carboxamido, sulphonyl and/or ester groups.

Polymers which can be used in particular are superabsorbers based on methacrylic acid or acrylic acid, polyvinyl alcohol/maleic anhydride copolymers, polysaccharide/maleic anhydride copolymers, maleic acid derivatives, acrylamidopropanesulphonic acid copolymers, starch/acrylonitrile graft polymers, gelatinized starch derivatives, alkyl- or hydroxyalkylcellulose, carboxymethylcellulose, starch/acrylic acid graft polymers, vinyl acetate/acrylic acid ester copolymers and copolymers of acrylonitrile or acrylamide.

The hydrogel used in the absorbent layer is, in particular, a water-insoluble polymer, the molecules of which are linked by ionic bonds to form a three-dimensional network. The hydrogel swells in contact with water with an increase in volume, but without losing material cohesion. The hydrogel of the absorbent layer is consequently capable of absorbing several times its own weight of liquids, such as water or aqueous salt solutions, including wound exudate.

In particular, the absorbent layer comprises at least one hydrophilic polymer or copolymer which is formed from monomers derived from acrylic acid. The hydrophilic polymers or copolymers preferably have sulphonyl side groups. It is furthermore preferable for at least some of these sulphonyl side groups to be present in their salt form, so that counter-cations which differ from H$^+$ are contained in the hydrogel.

The hydrogel of the absorbent layer particularly preferably includes a polymer or copolymer which is formed from monomers chosen from the group consisting of sodium 2-acrylamido-2-methylpropanesulphonate (NaAMPS), potassium 2-acrylamido-2-methylpropanesulphonate (AMPS-K), ammonium 2-acrylamido-2-methylpropanesulphonate (ammonium-AMPS), potassium 3-sulphonatopropylacrylate (SPAK), sodium 3-sulphonatopropylacrylate (NaSPA), acrylic acid or combinations thereof. The hydrogel of layer (b) most preferably includes a copolymer which is formed from a combination of (i) NaSPA and NaAMPS, (ii) SPAK and NaAMPS, (iii) NaAMPS and AMPS-K, (iv) NaAMPS and ammonium-AMPS or (v) NaAMPS and acrylic acid.

The hydrogel of the absorbent layer can furthermore include a crosslinking agent, such as e.g. tripropylene glycol diacrylate. The amount of the crosslinking agent can conventionally be about 0.01 to about 0.5 wt. %, based on the weight of the hydrophilic polymers or copolymers of layer (b). However, the degree of crosslinking should not be too high, in order to reduce the danger of the hydrogel breaking up on swelling.

The water content of the absorbent layer is preferably at least 20 wt. %, in particular at least 25 wt. % and very particularly preferably about 30 wt. %, based on the total weight of the absorbent layer.

To increase the strength and mechanical stability and to improve the handling of the absorbent layer and thus of the wound dressing according to the invention, in a further embodiment the absorbent layer can include a stabilizing structure chosen from the group consisting of a woven fabric, a nonwoven, a lattice, a net or combinations thereof. Preferably, the absorbent layer includes as a stabilizing structure a polyester woven fabric, in particular a polyester woven fabric having a weight per unit area of from about 10 to 25 g/m$^2$, particularly preferably about 18 g/m$^2$. The position of the stabilizing structure can be chosen as desired perpendicular to the plane of the layers of the wound dressing according to the invention. The stabilizing structure can be arranged inside the absorbent layer, i.e. embedded in the absorbent layer, or applied to one of the outer surfaces of the absorbent layer. The absorbent layer has, for example, a weight per unit area of from 1.7 kg/m$^2$ to 2.1 kg/m$^2$.

In one embodiment the peripheral edge of the absorbent layer lies directly adjacent to the peripheral edge of the entire wound dressing. In a preferred embodiment, however, the peripheral edge of the absorbent layer is formed at a distance from the peripheral edge of the wound dressing, i.e. in plan view the surface of the absorbent layer is smaller than the surface of the entire wound dressing and the absorbent layer is located in a central region of the wound dressing. In this embodiment an edge region of the wound dressing is thus free from the absorbent layer.

The covering layer of the wound dressing according to the invention preferably includes a polyurethane film. This polyurethane film can be in a form which is impermeable to water or permeable to water, and in particular is permeable to water. The thickness of the covering layer is preferably 10 to 70 µm, preferably 30 to 50 µm and particularly preferably about 30 µm.

In addition to the absorbent layer and covering layer, the wound dressing according to the invention can have further layers.

In one embodiment the wound dressing has an adhesive layer. If present, the adhesive layer extends in the form of an adhesive strip along the edge region of the wound dressing and is applied to the side of the antimicrobial layer facing away from the absorbent layer, the adhesive strip only partially covering the antimicrobial layer. In this manner, sticking of the patient's wound opening to the adhesive layer, which is conventionally covered by a central region of the wound dressing, and thus an unfavourable wound climate, are avoided. The wound dressing according to the invention thus preferably includes an adhesive layer in an edge region of the wound dressing.

In a particularly preferred embodiment the edge region of the wound dressing in which an adhesive layer is formed corresponds to the edge region of the wound dressing which is free from the absorbent layer.

The adhesive layer can be provided, for example, by using a polyacrylate adhesive, a silicone adhesive or a hydrocolloid adhesive. The adhesive layer particularly preferably comprises a water-containing hydrogel. The hydrogels described above in connection with the absorbent layer are in principle also suitable for use as a hydrogel in the adhesive layer. Very particularly preferably, the adhesive layer comprises an ionic copolymer of acrylic acid and a salt of acrylic acid, the content of acrylic acid units being about 2 wt. %.

In a further embodiment the adhesive layer can include a stabilizing structure chosen from the group consisting of a woven fabric, a nonwoven, a lattice, a net or combinations thereof. Preferably, the adhesive layer includes as a stabilizing structure a polypropylene woven fabric, preferably a polypropylene woven fabric having a weight per unit area of from about 15 to 25 $g/m^2$, particularly preferably about 20 $g/m^2$. The stabilizing structure is preferably embedded inside the adhesive layer and the position of the stabilizing structure can be chosen as desired within the adhesive layer, perpendicular to the plane of the layers of the wound dressing according to the invention.

According to an alternative embodiment, the wound dressing according to the invention has no separately configured adhesive layer. Rather, in this embodiment the absorbent layer extends over essentially the entire antimicrobial layer, i.e. over a central region and the edge region of the wound dressing. The material of the absorbent layer thereby partially or completely penetrates the antimicrobial layer. In this manner, during use of the wound dressing the absorbent layer can achieve an adhesive action and ensure secure and reliable fixing of the wound dressing on the patient. In particular, the antimicrobial layer is penetrated only partially, preferably in an edge region of the wound dressing, by the absorbent layer, so that sticking of the patient's wound opening, which is conventionally covered by a central region of the wound dressing, to the absorbent layer functioning as an adhesive layer and thus an unfavourable wound climate is avoided. According to this alternative embodiment, in which the absorbent layer extends over essentially the entire antimicrobial layer and penetrates this partially or over the entire cross-section, the thickness of the absorbent layer is conventionally somewhat smaller compared with an embodiment in which the absorbent layer extends only over a central region of the wound dressing and a separate adhesive layer is formed in the edge region.

In addition to the abovementioned layers, the wound dressing according to the invention can have a peelable protective layer. This is expediently adjacent to the hydrophobic antimicrobial layer or, if an adhesive layer is present, to the adhesive layer. The peelable protective layer preferably comprises siliconized paper or a suitable polymer, such as a siliconized polyester, e.g. siliconized polyethylene terephthalate. The peelable protective layer is expediently removed before the wound dressing according to the invention is used on the patient.

In a particularly preferred embodiment, the wound dressing according to the invention thus has the following layers in the following sequence: a covering layer, preferably a polyurethane film which is permeable to water; an absorbent layer which comprises at least one water-containing hydrogel, preferably a copolymer based on acrylic acid monomers with sulphonyl side groups having a water content of at least 20 wt. %, a polyester woven fabric having a weight per unit area of from about 10 to 25 $g/m^2$ preferably being embedded inside the hydrogel as a stabilizing structure, a hydrophobic antimicrobial layer, preferably a cellulose acetate fabric which is coated with DACC; optionally an adhesive layer, which preferably comprises a water-containing hydrogel, such as a copolymer based on acrylic acid monomers having a water content of at least 20 wt. %, a polypropylene woven fabric having a weight per unit area of from about 15 to 25 $g/m^2$ preferably being embedded inside the adhesive layer as a stabilizing structure; and optionally a peelable protective layer, which preferably comprises a siliconized polyethylene terephthalate.

In plan view the wound dressing according to the invention can have a rotationally symmetric base shape, for example the shape of a circle, an ellipse, a square or a regular rectangle, or any other shape. In one embodiment which is particularly suitable for use of the wound dressing in the region of the patient's sacrum, the wound dressing according to the invention has a heart-shaped base shape in plan view.

It has been found that due to its specific structure the wound dressing according to the invention can be laid particularly well around lines and tubes leading out of the body or into the body. A particular advantage of the wound dressing according to the invention is moreover that by swelling of the hydrogel of the absorbent layer due to absorption of exudate, it is capable of substantially completely covering the wound opening and thus of reliably closing the access to the body for e.g. bacteria. This advantage is achieved in particular by a wound dressing in which the absorbent layer extends directly to the incision of the wound dressing. By the swelling of the absorbent layer, an additional stabilizing of, e.g., the catheter is achieved and low shearing forces prevail within the wound dressing and with respect to a wound to be treated.

BRIEF DESCRIPTION OF THE DRAWINGS

The present invention is explained in the following with the aid of drawing showing number of preferred embodiments, wherein:

FIG. 1 shows a plan view of a first preferred embodiment;

FIG. 2 shows a section along line II-II from FIG. 1;

FIG. 3 shows a plan view of a second preferred embodiment;

FIG. 4 shows a plan view of a third preferred embodiment;

FIG. 5 shows a plan view of a fourth preferred embodiment;

FIG. 6 shows a plan view of a fifth preferred embodiment;

FIG. 7 shows a plan view of a sixth preferred embodiment;

FIG. 8 shows a plan view of a seventh preferred embodiment;

FIG. 9 shows a plan view of an eighth preferred embodiment;

FIG. 10 shows a plan view of a ninth preferred embodiment;

FIG. 13 shows a plan view of a twelfth preferred embodiment;

DETAILED DESCRIPTION OF PREFERRED EMBODIMENTS AND BEST MODE

Figure 12:
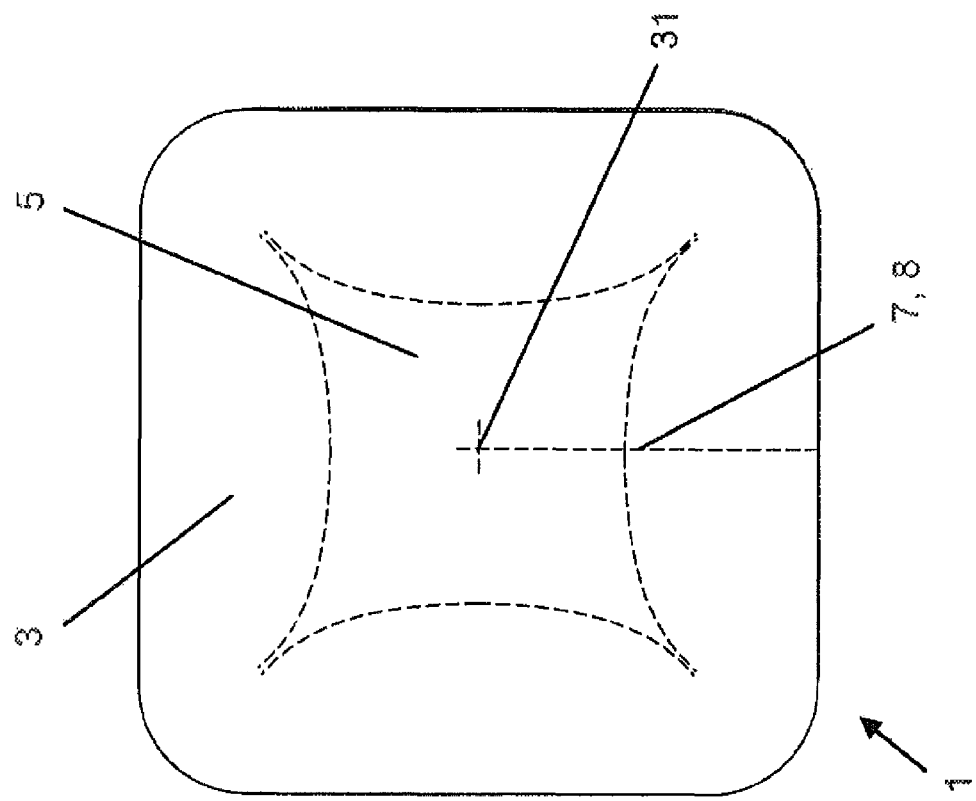
FIG. 12 shows a plan view of an eleventh preferred embodiment.

Referring now specifically to the drawings, FIG. 1 shows a wound dressing 1 according to the invention having an edge region 3 and a central region 5. The wound dressing furthermore has an incision 7. The incision 7 has a main section 8 which extends away from the edge. Two slits 9 extend away from the end 10 of the main section 8 remote from the edge, and together with the main section 8 form a Y-shaped incision 7 and thus, additionally to the main section 8, render possible a better fit of the wound dressing 1 according to the invention around e.g. a catheter tube. In one embodiment of the wound dressing, which is not shown, the slits 9 are not present at the end 10 of the main section 8 remote from the edge, so that the wound dressing has only a straight incision 7.

FIG. 2 shows a cross-section of the wound dressing 1 according to the invention according to FIG. 1 along line II-II. The wound dressing 1 has as the top layer a covering layer (c) 15, which extends over the entire cross-section. Underneath the covering layer 15 an absorbent layer (b) 17, which comprises a water-containing hydrogel, is configured in the central region 5 of the wound dressing 1. In the absorbent layer (b) 17 there is embedded a stabilizing structure 18 which leads to an increase in the strength and an improvement in the handling of the wound dressing. The edge region 3 of the wound dressing 1 is free from the absorbent layer 17. Below the absorbent layer 17 there is configured a hydrophobic antimicrobial layer (a) 19 which extends over the entire cross-section of the wound dressing 1. For fixing the wound dressing 1 on the patient, in the edge region 3 of the wound dressing 1 an adhesive layer 21 is formed as an adhesive strip in which a stabilizing structure 22 is embedded. The wound dressing 1 according to FIG. 1 furthermore has a peelable protective layer 23, which is applied to the side of the adhesive layer 21 facing away from the layer (a) 19.

The wound dressings shown in the following FIGS. 3 to 13 have essentially the same layer structure of wound dressing 1 as shown in FIG. 2. FIG. 3 shows a wound dressing 1 according to the invention which essentially corresponds to the embodiment of the wound dressing 1 shown in FIG. 1. In contrast to the wound dressing 1 according to FIG. 1, the wound dressing 1 according to FIG. 3 has a region 25 which is free from the absorbent layer 17. The absorbent layer 17 thus has a recess in the region 25 and the edges of the layer 17 which are adjacent to the region 25 are thus formed at a distance from one another. The incision 7 and the slits 9 of the wound dressing 1 are located in the region 25. The hydrogel-containing absorbent layer 17 thus does not extend to the incision 7 and the slits 9. The advantage of this is that the risk of parts of the hydrogel layer 17 becoming detached, for example by mechanical loads, after swelling of the layer and entering into the wound is reduced.

FIG. 4 shows a wound dressing 1 according to the invention in which a circular opening 29 is formed at the end of the incision 7 remote from the edge. Due to the circular opening 29 the wound dressing 1 can be fitted even more easily to the anatomy of the patient and the topography of the lines and tubes leading into the body or out of the body. The diameter of the circular opening 29 depends in particular on the diameter of the lines and tubes, such as e.g. catheters, used on the patient.

FIG. 5 shows a wound dressing 1 according to the invention having a region 25 in which the absorbent layer 17 has a recess. Three slits 31 which together with the main section 8 form a cross-shaped incision 7 are formed at the end of the main section 8 remote from the edge.

FIG. 6 shows a wound dressing 1 which corresponds to the wound dressing according to FIG. 5. Instead of the slits 31 arranged cross-shaped, the wound dressing 1 according to FIG. 6 has star-shaped slits 33.

FIG. 7 shows a wound dressing 1 having a region 25 in which the absorbent layer 17 has a recess. The incision 7 has a main section 8 which extends from the edge of the wound dressing 1 to an end 10 remote from the edge, the main section 8 has several transverse slits 35 running transversely to the main section 8.

FIG. 8 shows a wound dressing 1 according to the invention having a region 25 in which the absorbent layer 17 has a recess, the incision 7 having an opening 29 at the end remote from the edge and an opening 37 between the edge and the end of the incision 7 remote from the edge.

FIG. 9 shows a wound dressing 1 according to the invention having an incision 7 and a region 25, in which the absorbent layer 17 has a recess, an ellipsoidal opening 39 being formed at the end of the incision 7 remote from the edge.

FIG. 10 shows a wound dressing 1 according to the invention which corresponds to the wound dressing 1 according to FIG. 1. In contrast to the wound dressing 1 according to FIG. 1, the wound dressing 1 according to FIG. 10 has an ellipsoidal base area. The central region 5 of the wound dressing 1 accordingly also assumes an ellipsoidal form.

Figure 11:
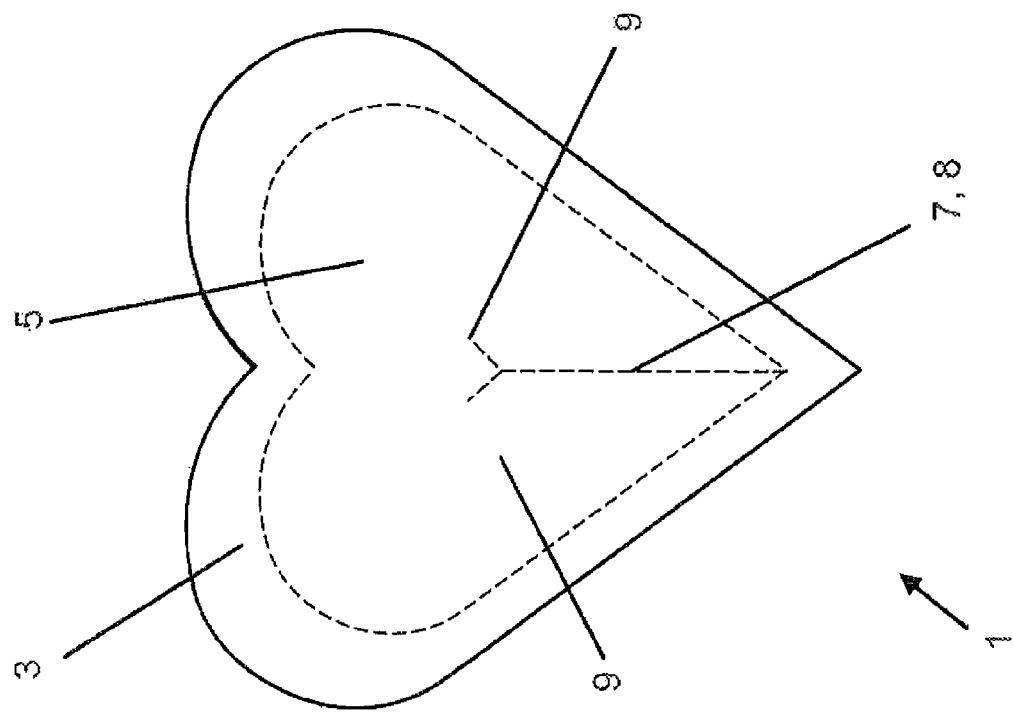
FIG. 11 shows a plan view of a tenth preferred embodiment.

FIG. 11 shows a wound dressing 1 according to the invention which corresponds to the wound dressing 1 according to FIG. 1. In contrast to the wound dressing 1 according to FIG. 1, the wound dressing 1 according to FIG. 11 has a heart-shaped base shape, as a result of which it is particularly suitable for covering wounds in the region of the sacrum.

FIG. 12 shows a wound dressing 1 according to the invention having an incision 7 and cross-shaped slits 31 at the end of the incision 7 remote from the edge. The central region 5 of the wound dressing 1 is star-shaped in structure, as a result of which the wound dressing is particularly suitable for covering wounds in the region of the bend of the elbow or of the buttocks.

FIG. 13 shows a wound dressing 1 according to the invention having an incision 7 which is formed as an elongated recess having two edges running at a distance from one another.

Figure 14:
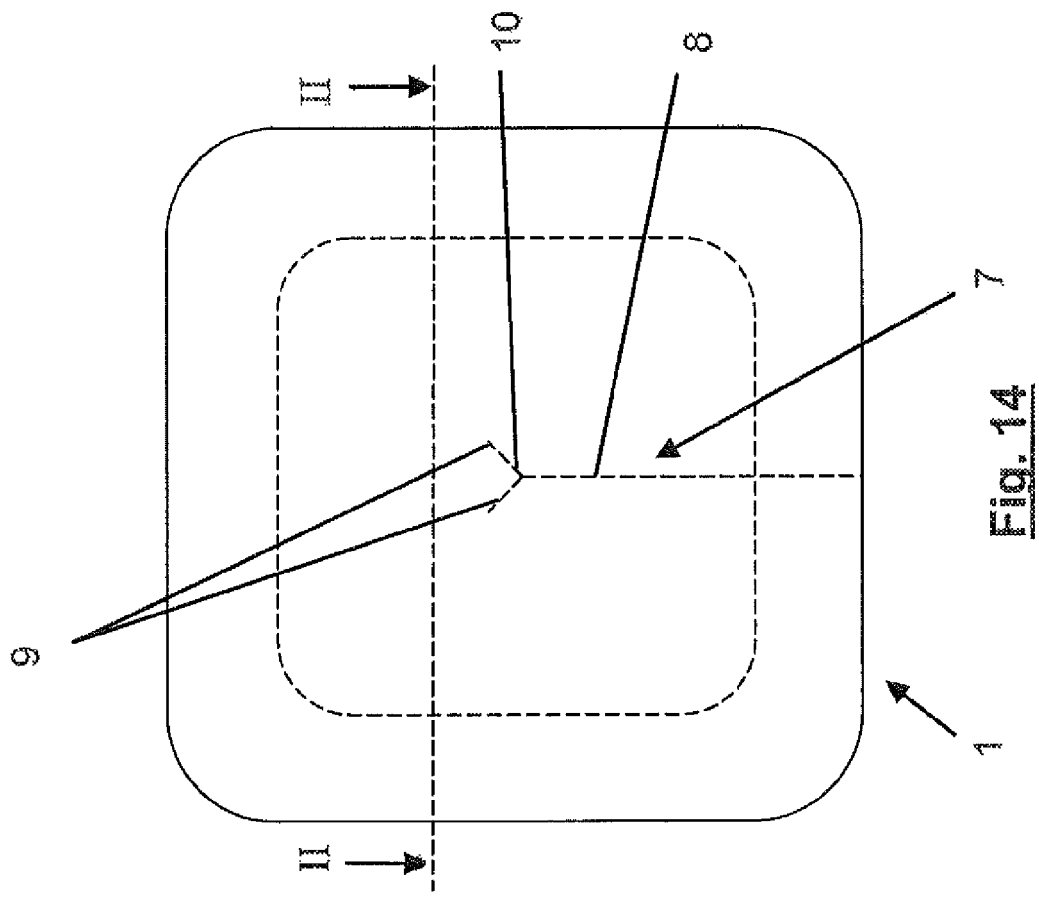
FIG. 14 shows a plan view of a thirteenth preferred embodiment.

FIG. 14 shows a wound dressing 1 according to the invention having an incision 7 which has a main section 8 extending away from the edge. Two slits 9 extend away from the end 10 of the main section 8 remote from the edge and together with the main section 8 form a Y-shaped incision 7.

Figure 15:
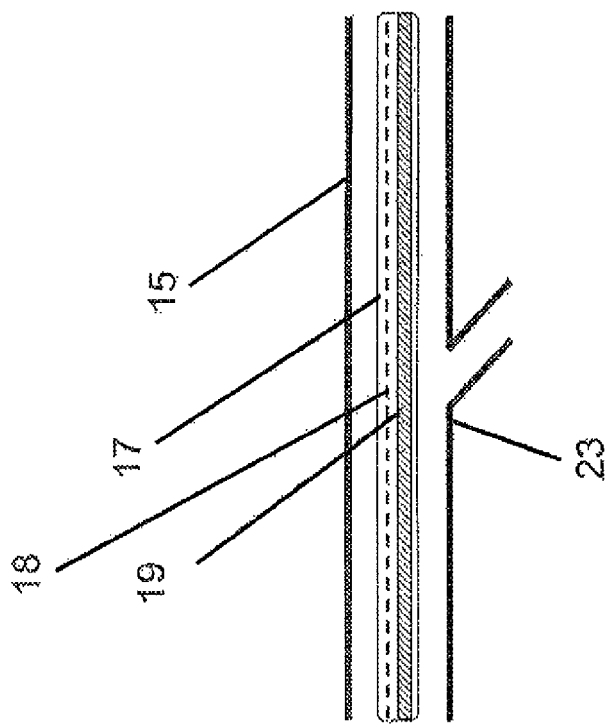
FIG. 15 shows a section along line II-II from FIG. 14.

FIG. 15 shows a cross-section of the wound dressing 1 according to the invention according to FIG. 14 along line II-II. The wound dressing 1 has as the top layer a covering layer (c) 15, which extends over the entire cross-section. Underneath the covering layer 15 an absorbent layer (b) 17, which comprises a water-containing hydrogel, extends over the entire cross-section of the wound dressing 1. In the absorbent layer (b) 17 there is embedded a stabilizing structure 18 which leads to an increase in the strength and an improvement in the handling of the wound dressing. To achieve an adhesive effect, the absorbent layer (b) 17 furthermore penetrates a hydrophobic antimicrobial layer (a) 19, which likewise extends over the entire cross-section of the wound dressing 1. The wound dressing 1 according to FIG. 14 furthermore has a peelable protective layer 23, which is applied to the side of the absorbent layer 17 facing away from the layer (c) 15.

A wound dressing according to several embodiments is described above. Various details of the invention may be changed without departing from the scope of the invention. Further more, the foregoing description of the preferred embodiments of the invention and best mode for practicing the invention are provided for the purpose of illustration only and not for the purpose of limitation, the invention being defined by the claims.

We claim:

1. A multilayered wound dressing having a peripheral edge, the multilayered wound dressing comprising:
    (a) a cover layer forming an outermost layer of the multilayered wound dressing and having an incision formed thereon that extends through an entire thickness of the multilayered wound dressing and separates the multilayered wound dressing;
    (b) at least one absorbent layer positioned beneath the cover layer in a center portion of the multilayered wound dressing such that the at least one absorbent layer extends directly into the at least one incision;
    (c) at least one hydrophobic antimicrobial layer positioned beneath the cover layer; and
    (d) an adhesive strip applied to a side of the antimicrobial layer facing away from the absorbent layer that extends along the peripheral edge of the adhesive strip only partially covering the antimicrobial layer, wherein:
    the at least one absorbent layer comprises a water-containing hydrogel having water-insoluble polymers that form a three-dimensional network that swells with an increase in volume when contacted with water and/or wound exudates.

2. The wound dressing according to claim 1, wherein the at least one incision comprises laterally adjacent edges extending along a length of the incision.

3. The wound dressing according to claim 1, wherein the at least one incision is formed as an elongated recess having laterally adjacent edges that are separated from one another.

4. The wound dressing according to claim 1, wherein the at least one incision has at least one opening between the peripheral edge and an end of the incision that is remote from the peripheral edge.

5. The wound dressing according to claim 1, wherein the at least one incision has an opening at an end of the incision that is remote from the peripheral edge.

6. The wound dressing according to claim 1, wherein the at least one incision has a main section that linearly extends from the peripheral edge to an end of the incision that is remote from the peripheral edge, the at least one incision further including one or more slits extending transverse relative to the main section of the incision.

7. The wound dressing according to claim 1, wherein the at least one incision has a main section that extends from the peripheral edge to an end of the incision that is remote from the peripheral edge, and further includes a plurality of slits extending away from the end of the incision that is remote from the peripheral edge.

8. The wound dressing according to claim 1, wherein the at least one hydrophobic antimicrobial layer comprises a cellulose acetate fabric, viscose fabric, cotton fabric or a blended fabric.

9. The wound dressing according to claim 8, wherein the at least one hydrophobic antimicrobial layer is treated with dialkylcarbamoyl chloride and/or alkene ketene dimer.

10. The wound dressing according to claim 1, wherein the at least one absorbent layer has a water content of at least 20 wt %.

11. The wound dressing according to claim 1, wherein the at least one absorbent layer comprises a polymer or copolymer which is formed from monomers chosen from the group consisting of sodium 2-acrylamido-2-methylpropanesulphonate (NaAMPS), potassium 2-acrylamido-2-methylpropanesulphonate (AMPS-K), ammonium 2-acrylamido-2-methylpropanesulphonate (ammonium-AMPS), potassium 3-sulphonatopropylacrylate (SPAK), sodium 3-sulphonatopropylacrylate (NaSPA), acrylic acid, or combinations thereof.

12. The wound dressing according to claim 1, wherein the cover layer comprises a polyurethane film.

13. The wound dressing according to claim 1, wherein the absorbent layer extends over and at least partially penetrates an entire length of the antimicrobial layer.

14. The wound dressing according to claim 1, further comprising a peelable protective layer.

* * * * *